(12) United States Patent
Brossier et al.

(10) Patent No.: US 10,302,550 B2
(45) Date of Patent: May 28, 2019

(54) PEELING TEST COUPON

(71) Applicant: Safran Aircraft Engines, Paris (FR)

(72) Inventors: Pascal Noël Brossier, Moissy-Cramayel (FR); Thibault Berranger, Moissy-Cramayel (FR); Emmanuel Chichery, Moissy-Cramayel (FR); Léa Gani, Moissy-Cramayel (FR); Alain Timon, Moissy-Cramayel (FR)

(73) Assignee: Safran Aircraft Engines, Paris (FR)

( * ) Notice: Subject to any disclaimer, the term of this patent is extended or adjusted under 35 U.S.C. 154(b) by 82 days.

(21) Appl. No.: 15/523,481

(22) PCT Filed: Nov. 5, 2015

(86) PCT No.: PCT/FR2015/053000
§ 371 (c)(1),
(2) Date: May 1, 2017

(87) PCT Pub. No.: WO2016/071647
PCT Pub. Date: May 12, 2016

(65) Prior Publication Data
US 2017/0307511 A1    Oct. 26, 2017

(30) Foreign Application Priority Data

Nov. 6, 2014   (FR) .................... 14 60740

(51) Int. Cl.
*G01N 19/04* (2006.01)
*G01M 5/00* (2006.01)
*G01N 33/00* (2006.01)

(52) U.S. Cl.
CPC .......... *G01N 19/04* (2013.01); *G01M 5/0016* (2013.01); *G01M 5/0075* (2013.01);
(Continued)

(58) Field of Classification Search
None
See application file for complete search history.

(56) References Cited

U.S. PATENT DOCUMENTS 5,317,925 A * 6/1994 Hayashi ............... G01N 3/08
422/53
5,626,462 A * 5/1997 Jackson ............... C22C 32/00
416/229 A (Continued)

FOREIGN PATENT DOCUMENTS

DE       90 13 935 U1   12/1990
DE       90 17 803 U1    4/1992
EP       2 549 263 A2    1/2013

*Primary Examiner* — Paul M. West
*Assistant Examiner* — Mark A Shabman
(74) *Attorney, Agent, or Firm* — Blank Rome LLP

(57) ABSTRACT

A coupon suitable for peeling tests, derived from a vane and including: (i) a portion of blade that comprises an intrados surface, an extrados surface and a leading edge and/or trailing edge and (ii) a vane reinforcement that covers and is glued to at least a part of the intrados surface, a part of the extrados surface and which extends beyond the leading and/or trailing edge. The reinforcement is split over the entire length of the leading edge and/or trailing edge such that the reinforcement is separated into two plates separate from one another and facing each other on either side of the slit beyond the leading and/or trailing edge. Furthermore, at least one of the plates furthermore comprises, beyond the leading and/or trailing edge, notches configured to provide a hold to this same plate.

6 Claims, 2 Drawing Sheets

(52) U.S. Cl.
CPC ............... *G01N 2033/0003* (2013.01); *G01N 2203/0091* (2013.01); *G01N 2203/027* (2013.01); *G01N 2203/0262* (2013.01); *G01N 2203/0298* (2013.01)

(56) References Cited

U.S. PATENT DOCUMENTS

| | | | |
|---|---|---|---|
| 7,028,555 B1* | 4/2006 | Logan | B60C 23/0493 73/150 A |
| 8,215,181 B1* | 7/2012 | Helmink | G01M 5/0016 73/760 |
| 2005/0111966 A1* | 5/2005 | Metheny | F01D 5/183 415/116 |

* cited by examiner

PEELING TEST COUPON

BACKGROUND OF THE INVENTION

1. Field of the Invention

The invention relates to an innovative peeling test device, particularly suitable for tests of coupons derived from vanes. Furthermore, the invention also concerns an innovative method of design of such test coupons that will be particularly suitable for the described device. Finally, the invention includes the manufacturing method of such coupons in addition to the method of implementing the assembly.

2. Description of the Related Art

Described below, with reference to FIG. 1, is a peeling test device comprising the latter's test coupon, already known, in accordance with the recommendations set out in standard NF EN 1464.

Hence, according to the known state of the art, a peeling test device comprises a frame 10 on which a pendulum 14 is suspended, around a pivoting link 12 with a horizontal axis 12a, comprising a front roller 16 and a guide roller 18, the respective axes 16a and 18a of which are parallel to the axis 12a. The angle between the directions (16a; 18a) and (18a; 12a) is 90°. The distances [16a; 18a] and [18a; 12a] are equivalent to 33 mm respectively.

Means of attachment 20 are arranged under the pendulum 14 and are connected to means of traction 22 configured to pull the means of attachment 20 vertically downwards, in a direction 22a passing through the pivot axis 12a. A force sensor 24 is inserted between the means of attachment 20 and the means of traction 22, capable of measuring the traction force exerted between the means of traction 22 and the means of attachment 20, i.e. the traction force in the downwards direction of the means of attachment 20.

A coupon 26 is used. The latter comprises a support 28, flat and rectangular in shape, in addition to an adhesive 30 glued to one surface of the support 28. The coupon is positioned on the two front and guide rollers 16, 18 in its length, with the adhesive 30 facing downwards resting on the rollers and a portion of the end 32 of the adhesive 30 is pre-detached and made accessible between the two rollers 16, 18. The means of attachment 20, in this case jaws, are attached by clamping to the end 32 of the adhesive 30.

In order to start the peeling test, the means of traction 22 are operated with a constant displacement speed constraint and the values transmitted by the force sensor 24 are recorded. When the means of traction 22 are operated, the end 32 of the adhesive 30 deforms and is stretched downwards. The adhesive 30 gradually detaches itself from the support 28, along a peeling front and is drawn downwards tangentially to the front roller 16, whilst the support 28 moves by rolling from the front roller 16 to the guide roller 18.

During peeling, the pendulum 14 rotates around the pivot 12 until the surface of the front roller 16 is tangent to the pulling direction 22a at the vertical of the pivot axis 12a.

Although this peeling test device is very well suited to coupons performed specifically with simple geometries, it is not however suitable for coupons with more complex shapes, such as those displaying variable curvatures for each of their faces, variable thicknesses and non-parallel faces. Indeed, in order to validly analyze all the peeling tests, the peeling angle, i.e. the angle between the surface of the support on which the peeling front is located and the pulling direction of the adhesive must remain identical for all the peeling tests performed on the different coupons. This is not possible with complex and variable coupons such as those mentioned above.

SUMMARY OF THE INVENTION

Starting from the above observation, the invention provides a simple, efficient and economical solution making it possible to perform peeling tests observing the defined norms on complex-shaped coupons.

For this purpose, it provides for a peeling test device, designed to test the resistance to peeling of coupons each consisting of a support and an adhesive glued to a support surface and comprising:

a frame comprising a front roller and at least one guide roller, with parallel axes designed to maintain the coupon supported while guiding movement of the latter, tangentially to the rollers by rolling, during the peeling test, means of attachment designed to be attached with the adhesive, means of traction linked to the means of attachment, configured in order to pull the means of attachment in a pulling direction tangential to the front roller and designed to cause detachment of the adhesive from the surface of the support, means of measuring the force exerted by the means of traction in order to pull the means of attachment during peeling, characterised in that at least one of the rolls is translationally adjustable in relation to the other rolls in a direction perpendicular to the axes of the rolls.

The possibility offered by the invention of moving at least one of the rollers among the front or guide rollers in relation to the frame makes it possible to change the position of the coupon in relation to the frame before beginning the peeling test or during the peeling test.

In order to function, the coupon must rest with its face comprising the adhesive against the front roller. It is tangentially to this roller that the adhesive is drawn away from the support in order to detach it from the support, according to a predetermined angle in relation to the surface of the support known as the peeling angle. Hence, during peeling, the adhesive detaches itself from the support and skirts the front roller whereas the support is wound on the rollers. The peeling test tends to cause the coupon to pivot around the front roller. This is the reason why the guide rollers are provided to keep the orientation of the coupon constant in relation to the frame.

In a first case, the coupon can be retained by the guide rollers by its face comprising the adhesive to be peeled. In this case, at least one guide roller needs to be positioned downstream from the peeling front, i.e. on the side of the peeling front created opposite the front roller. The coupon is in this case pushed by the front and guide rollers.

In a second case, the coupon can be retained by the guide rollers by its face opposite the adhesive to be peeled. In this case, at least one guide roller needs to be positioned upstream from the peeling front, i.e. on the same side of the peeling front created as the front roller. The coupon is in this case housed between the front and guide rollers.

Coupons with different respective curvatures, or different respective thicknesses, resting on rollers that are not adjustable in relation to the frame, during tensioning of the means of traction and of the adhesive, would have different respective orientations in relation to one another in the perpendicular plane to the axes of the rollers during successive peeling tests. The peeling angles for the different tests would therefore all be different and the tests would not be comparable with each other. On the other hand, the inclination of the coupon can be varied by changing the position of one of the rollers as indicated by the invention. This is of obvious value, since translationally adjusting the rollers makes it possible to obtain an orientation of the coupons, tangentially in relation to the front roller, which is always identical. The different peeling tests carried out are therefore performed according to the same peeling angle and are therefore comparable with each other.

Likewise, if the curvature of the coupon is variable over its extent, it is also possible to vary the position of one of the rollers during the peeling test, while the coupon progresses tangentially in relation to the rollers, in order to maintain the same peeling angle throughout the entire test.

According to one characteristic of the invention, the guide rollers each have an external local annular bearing surface with a linear appearance.

This characteristic can be achieved for example if the external bearing surface is elliptical in appearance, for example spherical or moreover toric. Owing to this characteristic, the entire circumference of the roller has a bearing surface that makes it possible to obtain a one-off connection with an opposite flat surface.

This characteristic is functional and offers an advantage, as explained below, in combination with and independently from the characteristic according to which at least one of the rollers is translationally adjustable in relation to the other rollers in a direction perpendicular to the axes of the rollers.

It is therefore possible to consider as an invention in its own right a peeling test device, designed to test the resistance to peeling of coupons each consisting of a support and an adhesive glued to a support surface and comprising a frame comprising a front roller and at least one guide roller, with parallel axes designed to maintain the coupon supported while guiding movement of the latter, tangentially to the rollers by rolling, during the peeling test, means of attachment designed to be attached with the adhesive, means of traction linked to the means of attachment, configured in order to pull the means of attachment in a pulling direction tangential to the front roller and designed to cause detachment of the adhesive from the surface of the support, means of measuring the force exerted by the means of traction in order to pull the means of attachment during peeling, characterised in that the guide rollers each have an external local annular bearing surface with a linear appearance.

Indeed, a device of this kind offers an advantage when a coupon has a face on which the adhesive is glued not parallel to its opposite face and/or twisted over its length. Under such circumstances, if one of the guide rollers were to have a linear connection with the coupon, by having a cylindrical or truncated cone-shaped surface for example, with an axis parallel to the front roller, the front roller would not be able to rest stably on such a coupon. If however the guide rollers are formed in order to create a one-off connection regardless of the angular position of the roller, the surface of the coupon bearing the adhesive will be able to rest completely against the front roller, whereas the remainder of the coupon will be able to pivot around isolated contacts of the guide rollers.

Advantageously, the means of attachment comprise a cable designed to engage around the adhesive of the coupon. Such a cable may be simultaneously sufficiently fine, supple and strong, made of Kevlar™ for example, which fully meets the requirements in terms of flexibility and solidity of the means of attachment.

Preferentially, the front roller is translationally adjustable in relation to the frame in a direction parallel to the pulling direction and one of the guide rollers is translationally adjustable in relation to the frame in a direction perpendicular to the pulling direction.

The front roller is translationally adjustable in relation to the frame in a direction parallel to the pulling direction to allow the front roller to remain tangent to the pulling direction even after its adjustment, which is necessary for proper functioning of the device and compliance with the peeling norm. Starting from such observation, allowing a guide roller to be translationally adjustable in a direction perpendicular to the pulling direction makes it possible to maximise the possibilities for orientation of the coupon.

To be more precise, the pulling direction is fixed in relation to the frame and the front roller is only translationally adjustable in relation to the frame in a direction parallel to the pulling direction. It is indeed safer to propose a constantly fixed pulling direction, since in this case, there is no risk of a change in the pulling direction during the tests. Even though it remains possible to produce a device in which the pulling direction can be adjustable, in order to vary the peeling angle, such a device will be much more costly and complex to realise, whereas the invention as described above already provides satisfaction answers to the problems of adjusting the peeling angle.

In a preferred embodiment, the front roller has a cylindrical surface.

In test position, such a device will advantageously comprise a coupon with a complex shape, for example curved variably or regularly over its length and/or with non-parallel opposite faces and/or with a variable thickness, the surface to which adhesive is applied of which rests on the front roller, according to a plane tangent to the front roller which forms a predetermined angle with the pulling direction, preferably 90°. This peeling angle is very extensively used for the peeling tests and therefore allows comparison of the tests performed with many other tests.

Furthermore, when the coupon is directly derived from vanes used in aeronautics for example, the adhesive does not necessarily have a free end easily grasped by the means of attachment of the peeling test device. Indeed, such a vane comprises a blade equivalent to the test coupon support and a reinforcement equivalent to the adhesive of the test coupon. The reinforcement generally covers the upstream parts of the extrados and intrados surfaces of the blade, in addition to the leading edge of the blade. Cuts are performed in the reinforced vane in order to extract from the latter these coupons, which will allow testing of retention of the reinforcement on the blade. It is in particularly interesting to test the resistance to detachment of the reinforcement from the leading edge of the blade, since this is the scenario most likely to occur during actual functional use of the vane, for example in case of collision with an object originating upstream from the blade. Since the reinforcement does not have any part that can be grasped on the leading edge of the blade and since it is both glued to the extrados and intrados surfaces of the blade, it is currently impossible to perform a utilisable peeling test.

This is why the invention also concerns, regardless of the peeling test device, a coupon, suitable for peeling tests, derived from a vane and comprising a portion of blade of the vane that comprises a intrados surface, a extrados surface and a leading and/or trailing edge and a vane reinforcement that covers and is glued to at least a part of the intrados surface, a part of the extrados surface and which extends beyond the leading and/or trailing edge, characterised in that the reinforcement is split over the entire length of the leading and/or trailing edge such that the reinforcement is separated into two plates separate from one another and facing each other on either side of the slit beyond the leading and/or trailing edge, and in that at least one of the plates furthermore comprises, beyond the leading and/or trailing edge, fastening means providing a hold to this same plate.

In particular, the vane may be derived from a turbine engine vane.

It is emphasised that the coupon defined above is to be considered an invention in itself, since it provides an exhaustive solution to the problem of peeling of coupons derived from vanes. Moreover, it is not limited to the peeling test device described in this document.

A solution has been found here that allows performance of useful peeling tests on coupons derived from vanes, since, owing to the slit, the reinforcement has been separated into two distinct plates, one glued to the intrados surface of the blade and the other glued to the extrados surface of the blade. Each of these plates retains however a portion extending beyond the leading edge of the blade. This same portion has been prepared such as to comprise fastening means adapted to the means of attachment of the peeling test device.

It will also be noted that such a coupon is perfectly suited to the peeling test device according to the invention described above, since it will be complex in shape, with non-parallel surfaces (the intrados and extrados surfaces) in addition to its own potentially variable thickness and curvature, wherein these specificities are inherited from the vane from which the coupon is formed.

Advantageously, the fastening means comprise notches formed on opposite edges of the plate. These fastening means are adapted to the cable of the peeling test described above, since the cable can be looped around the portion of plate protruding from the leading edge of the blade, while passing through the notches in order to ensure a reliable hold. This embodiment is particularly interesting, since it allows the cable to have a well distributed hold on the plate.

It will be possible, similarly, to pierce the plate with a hole designed to receive an end of a cable. In this case, the cable may for example be secured in its position by a thick lock fixed to its end and will thus be unable to pass back through the hole in the plate.

The blade will comprise for example an organic matrix composite and the reinforcement will comprise for example titanium. This corresponds to the circumstances most likely to be encountered.

Preferentially, the intrados and extrados faces are not parallel, with the thickness between these faces and their respective curvatures being furthermore variable along the blade.

As already mentioned above, such coupons are directly derived from vanes used in aeronautics and therefore allow their behaviours to be simulated as closely as possible.

The invention furthermore relates to a method of manufacturing a coupon as described above, comprising the stages involving supplying a vane comprising a blade which comprises an intrados surface, an extrados surface, a leading edge and a trailing edge and comprising a single-section reinforcement that covers and is glued to at least a part of the intrados surface, a part of the extrados surface and the entire leading edge or trailing edge, sampling a portion of this vane, wherein the portion comprises at least a part of the leading or trailing edge of the blade covered with the reinforcement, splitting the reinforcement over the entire length of the leading or trailing edge such that the reinforcement is separated into two plates separate from one another and facing each other on either side of the slit beyond the leading or trailing edge of the blade and forming on at least one of the plates, beyond the leading or trailing edge of the blade, fastening means providing a hold to this same plate.

The fastening means may therefore consist of notches formed on opposite edges of the plate.

The invention also relates to a peeling test device as described above, furthermore comprising a peeling test coupon derived from a vane as proposed above, wherein the coupon is held against the rollers and is capable of being guided in movement tangentially in relation to the latter by rolling and the means of attachment are engaged with the fastening means of one of the plates of the coupon resting on the front roller.

This type of device is fully functional and allows performance of perfectly utilisable peeling tests, as could be explained above, on coupons derived directly from reinforced vanes.

Preferentially, the device is configured in this case in order to obtain a peeling angle of 90°.

The invention finally relates to a method of initialising the peeling test device comprising a coupon, comprising the stages involving:

adjusting the position of the rollers by translation such that the coupon, when held against the rollers, has a direction of movement tangentially in relation to the front roller separated angularly from the pulling direction by a previously chosen peeling angle, positioning the coupon resting against the rollers such that one of the ends of the adhesive projects from the front roller on the side on which the pulling direction and therefore the means of attachment are located.

For a coupon derived from a vane as described above, one of the plates of the coupon will be positioned resting on the front roller such that the fastening means of this same plate of the coupon project from the front roller on the side on which the pulling direction is located. It will subsequently be possible to engage the means of attachment with the fastening means of the coupon.

If necessary, depending on the shape of the coupon, this method may be followed by a stage involving adjusting the position of the rollers by translation during the test, during pulling of the means of attachment and therefore movement of the coupon tangentially in relation to the roller, such that the coupon remains tangential in relation to the front roller in a constant plane throughout the entire duration of the peeling test.

BRIEF DESCRIPTION OF THE DRAWINGS

The invention will be better understood, and other details, characteristics and advantages of the invention will appear upon reading the following description given by way of a non-restrictive example while referring to the appended drawings wherein.

DETAILED DESCRIPTION OF THE PREFERRED EMBODIMENTS

Figure 1:
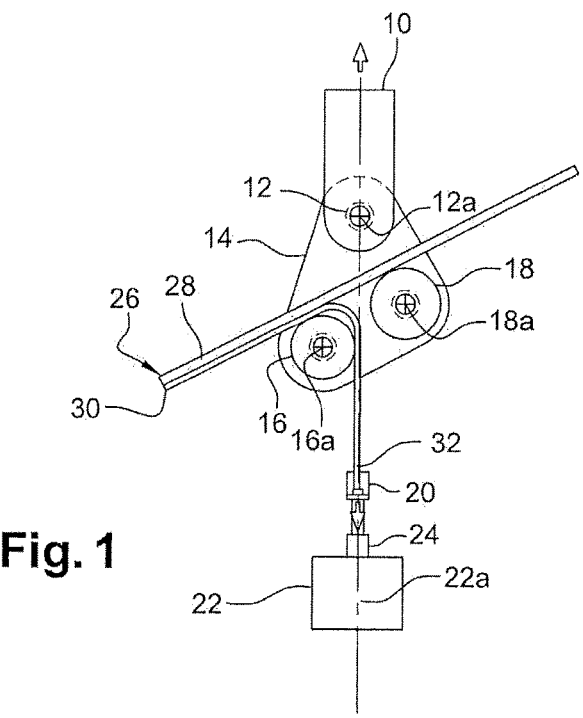
FIG. 1, already described, shows a diagrammatic view of a peeling test device according to the proposals of standard NF EN 1464.
Figure 2:
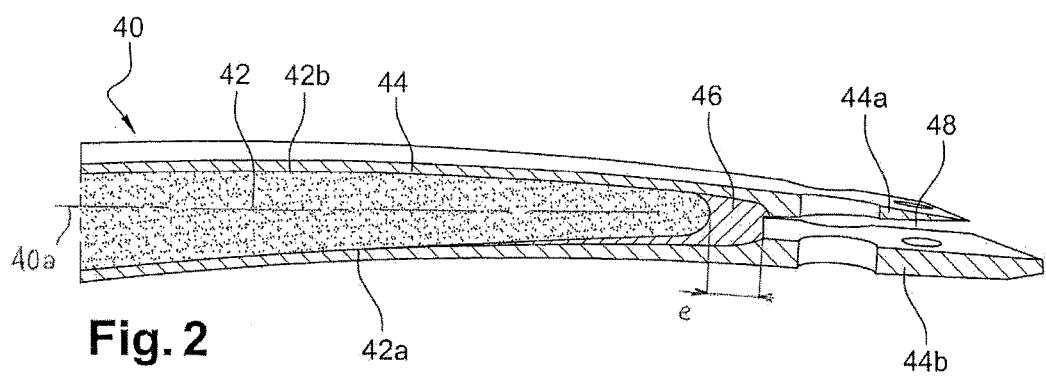
FIGS. 2 and 3 show side and front views of a peeling test coupon derived from a vane, according to the invention.
Figure 3:
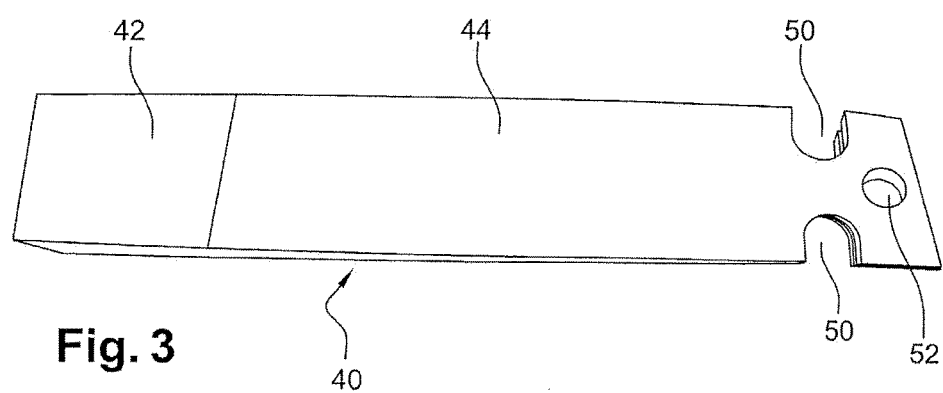

According to FIGS. 2 and 3, a coupon 40 derived from a vane can be seen, which has been cut along planes perpendicular to its leading edge. Such a vane comprises a blade 42 made of organic matrix composite material, which forms the support for the coupon according to the invention. It also comprises a reinforcement 44, made of titanium, which covers the upstream part of the vane and which constitutes the adhesive of the coupon according to the invention. In the following, reference will be made to the coupon, by continuing to use the notion of blade to designate the support and the notion of reinforcement to denote the adhesive. As can be seen, the blade presents an intrados surface 42a, an extrados surface 42b and a leading edge 46, from which the reinforcement 44 projects. The leading edge 46 is metallic. It may be made of titanium. Its thickness e along the general axis 40a of elongation of the coupon 40 will typically be included between 50 and 100 mm. The glued intrados and extrados surfaces of the reinforcement 44 are curved differently from one another and the thickness of the blade 42 varies between these surfaces. Although the reinforcement 44 is originally formed of a single piece covering the entire leading edge 46 of the blade, in addition to a part of its intrados and extrados surfaces, the reinforcement comprises at this point a through slit 48 exposing the entire leading edge 46 of the coupon blade. In this way, the reinforcement 44 is separated into two distinct plates 44a and 44b facing each other on either side of the slit 48 beyond the leading edge 46. The reinforcement 44 still extends however over the entire width of the coupon, even if it is not present up to the trailing edge of the blade 42.

The plates 44a and 44b comprise, between the leading edge 48 of the blade and its end, opposite and substantially symmetrical notches 50 machined on their side edges. These notches 50 serve as holds for a looped cable that can be passed through the slit 48 between the plates 44a and 44b and subsequently engaged in the notches 50. Alternatively, the plates 44a, 44b comprise, beyond the leading edge 46, respective holes 52 that may also serve to provide a hold; for example by inserting and blocking the end of a cable.

The vane thus cut and prepared becomes a coupon utilisable for peeling tests, since it comprises a separate adhesive on each of its faces, embodied by each plate 44a, 44b, one end of which is freed from the support, embodied by the blade 42 and features fastening means 50, 52 that can be easily grasped.

Figure 4:
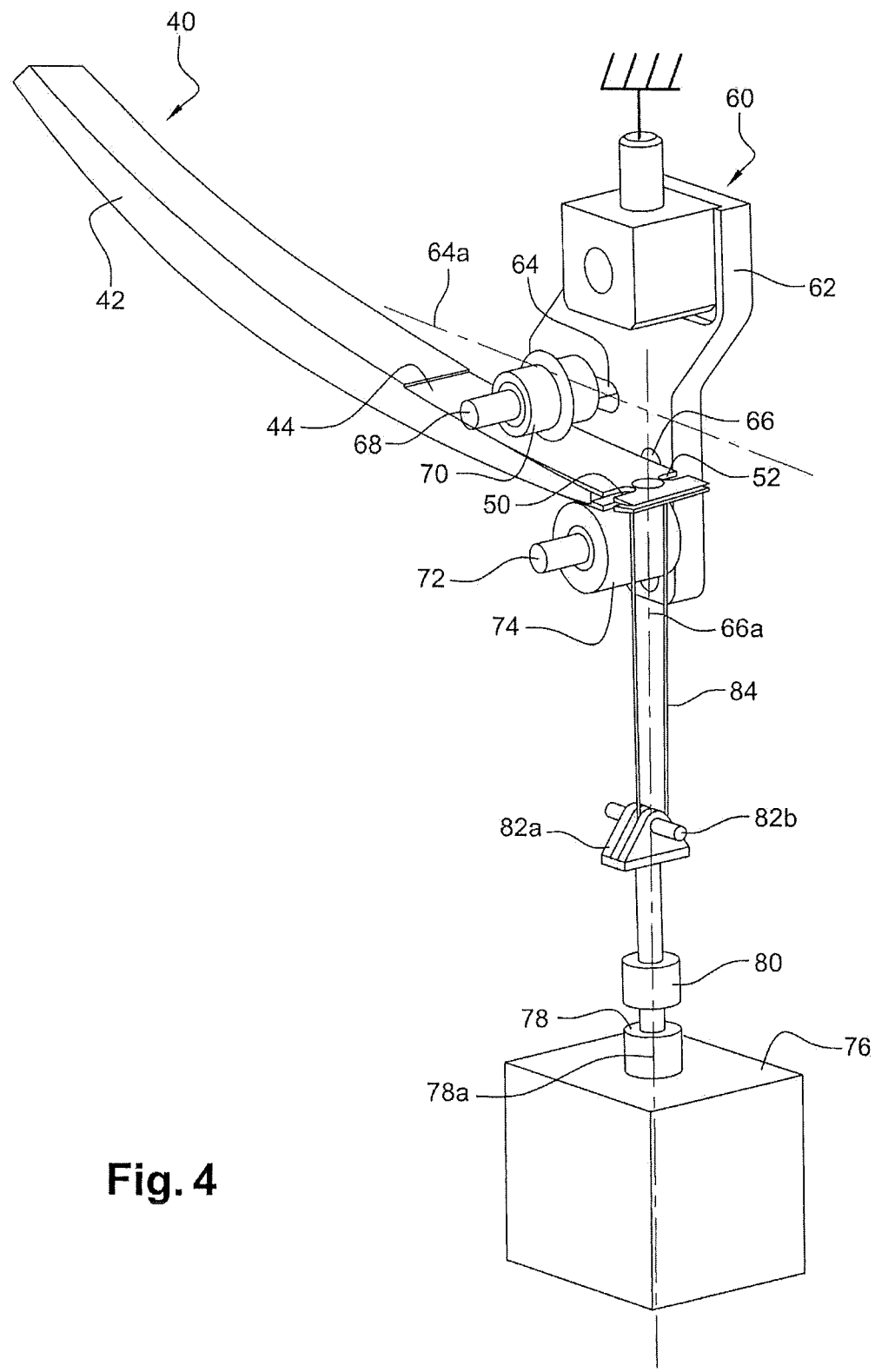
FIG. 4 shows a perspective diagram of a peeling test device according to the invention.

By reference to FIG. 4, an example of a peeling test device according to the invention is described, comprising the coupon illustrated in FIGS. 2 and 3. As explained above, the peeling test device according to the invention can be used with a wide range of coupons with complex or simple shapes, other than that shown here.

A frame 60 is fixed. This frame comprises a vertical wall 62 comprising two lumens 64, 66, one 64 oblong in shape with a major horizontal axis 64a and the other 66 substantially isometric with a major vertical axis 66a. The dimensions of the two lumens may however be entirely different.

The lumen 64 serves for passage of a shaft 68 perpendicular to the wall 62, with a diameter corresponding to the minor axis of the lumen 64. This shaft 68 is translationally adjustable in the lumen 64 in the horizontal direction of the major axis 64a. A hollow guide roller 70 is mounted on the shaft 68 on one side of the wall 62. This roller is free to rotate around the shaft 68. The guide roller 70 has an external local annular bearing surface with a linear appearance, as described in detail above in this document. Although illustrated in the figure as having a toric surface, the roller 70 might therefore equally have a completely spherical surface for example.

The lumen 66 serves for passage of a shaft 72 perpendicular to the wall 62, with a diameter corresponding to the minor axis of the lumen 66. This shaft 72 is translationally adjustable in the lumen 66 in the vertical direction of the major axis 66a. A hollow front roller 74 is mounted on the shaft 72 on the same side of the wall 62 as the guide roller 70. This front roller is free to rotate around the shaft 72. The front roller 74 has a cylindrical surface.

The guide roller 70 is in translation throughout its entire adjustment range, offset horizontally and vertically from the front roller 74.

A second wall, not illustrated in the figures, is conventionally fixed opposite the first wall 62 on the other side of the rollers. This second wall comprises lumens symmetrical to the lumens 64, 66 of the first wall 62 in which the shafts 68, 72 are secondarily supported on the other side of the rollers. The loads are thus distributed equally over the shafts on either side of the rollers 70, 74, which are subject to transversal stresses during operation. This avoids distortion of the shafts.

Means of traction 76 are located under the frame 60, comprising a vertical jack 78, a vertical axis 78a tangent to the surface of the front roller 74, on the side of the front roller opposite the guide roller 70. A force sensor 80 is incorporated in the jack 78 and measures the vertical traction force exerted by the jack. It should be noted that the force sensor may equally be mounted anywhere along the traction chain. A yoke 82a and axis 82b assembly is arranged on the top end of the jack 78. A cable loop 84, made for example of Kevlar™, i.e. poly (p-phenylene terephthalamide), is mounted in the yoke 82a and around the axis 82b.

The coupon 40 described while referring to FIGS. 3 and 4 has been arranged between the guide roller 70 and the front roller 74. The split end of the reinforcement 44 slightly projects from the front roller 74. The loop 84 is engaged in the slit 48 of the coupon and in the notches 50, such that one of the plates 44b is engaged with the loop 84.

The loop 84 is tensioned by the jack 78 and presses the lower face of the coupon 40 against the front roller 74. The coupon subsequently tends to pivot around the front roller 74 and its upper face is pressed against the guide roller 70. It is therefore clearly seen that the coupon will not have the same orientation depending on the relative position of the two rollers. On the other hand, regardless of the position of the front roller 74 in the vertical lumen 66, the loop 84 will always be tensioned vertically and tangentially in relation to the front roller 74.

During operation, the loop 84 pulls the plate 44b downwards and detaches the latter from the blade 42. The coupon 40 is free to move by rolling along the rollers 70, 74, such that the rolling front is always located substantially at the vertical of the loop 84. The peeling test is performed by recording the data delivered by the force sensor 80 when the jack 78 moves downwards at constant speed.

It is easy to automate the translational movement of the rollers 70, 74 in the lumens 64, 66 during movement of the jack 78, so that at all times, depending on the variations in curvature and thickness of the coupon 40, the orientation of the coupon tangentially to the front roller 74 is maintained.

It will of course be possible to modify the attachment system consisting of the notches 50, the loop 84, the yoke 82*a* and the axis 82*b* by any other known attachment system capable of effectively grasping the coupon adhesive and pulling the latter downwards.

The invention claimed is:

1. A coupon suitable for peeling tests, wherein the coupon is sampled from a vane so that the coupon comprises a portion of said vane having a portion of a blade of the vane that comprises an intrados surface, an extrados surface and at least one of a leading edge and a trailing edge and which is covered by a vane portion reinforcement which is glued to at least a part of the intrados surface, a part of the extrados surface, and which extends beyond said at least one of the leading and the trailing edge, wherein the vane portion reinforcement is split over the entire length of said at least one of the leading edge and the trailing edge, so that the vane portion reinforcement is separated into two plates separate from one another and facing each other on either side of a slit beyond said at least one of the leading and the trailing edge of the vane position, and wherein at least one of the plates furthermore comprises, beyond said at least one of the leading and the trailing edge, fastening means providing a hold to said at least one of the plates for traction.

2. The coupon according to claim 1, wherein the fastening means comprise notches formed on opposite edges of the plate.

3. The coupon according to claim 1, wherein the intrados and extrados surfaces are not parallel, with the thickness between these surfaces and their respective curvatures being furthermore variable along the blade.

4. The coupon according to claim 1, wherein the blade comprises an organic matrix composite and the reinforcement comprises titanium.

5. The coupon according to claim 1, wherein the coupon is derived from a turbine engine vane.

6. A method of manufacturing a coupon according to claim 1, the method comprising:

supplying the vane comprising:
the blade that comprises intrados surface, the extrados surface, the leading edge and the trailing edge and
the vane portion reinforcement formed of a single piece that covers and is glued to at least the part of the intrados surface, the part of the extrados surface and the entire one of the leading and the trailing edge, sampling a portion of this vane, wherein the portion comprises at least a part of said at least one of the leading edge and trailing edge of the blade covered with the reinforcement, splitting the vane portion reinforcement over the entire length of said at least one of the leading and the trailing edge such that the vane portion reinforcement is separated into the two plates separate from one another and facing each other on either side of the slit beyond said at least one of the leading and the trailing edge of the blade and forming on at least one of the plates, beyond said at least one of the leading and the trailing edge of the blade, the fastening means providing a hold to said at least one of the plates for means of attachment, for the purpose of traction.

* * * * *